(12) United States Patent
Grant et al.

(10) Patent No.: US 8,414,536 B2
(45) Date of Patent: *Apr. 9, 2013

(54) PUMP ASSEMBLY WITH A REMOVABLE COVER ASSEMBLY

(75) Inventors: Kevin L. Grant, Litchfield, NH (US); Marc A. Mandro, Bow, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/230,110

(22) Filed: Sep. 12, 2011

(65) Prior Publication Data

US 2012/0004609 A1    Jan. 5, 2012

Related U.S. Application Data

(63) Continuation of application No. 12/249,496, filed on Oct. 10, 2008, now Pat. No. 8,016,789.

(51) Int. Cl.
*A61M 1/00* (2006.01)
(52) U.S. Cl. .......................... 604/151; 604/114
(58) Field of Classification Search ............... 417/4, 31, 417/39, 41–45; 604/65–67, 111, 114, 134–139, 604/151–155
See application file for complete search history.

(56) References Cited

U.S. PATENT DOCUMENTS

| | | | | |
|---|---|---|---|---|
| 5,718,562 | A * | 2/1998 | Lawless et al. ................... | 417/1 |
| 5,989,227 | A | 11/1999 | Vetter et al. | |
| 6,305,908 | B1 * | 10/2001 | Hermann et al. .............. | 417/234 |
| 7,390,314 | B2 | 6/2008 | Stutz, Jr. et al. | |
| 8,016,789 | B2 * | 9/2011 | Grant et al. ................... | 604/151 |
| 2007/0100283 | A1 | 5/2007 | Causey, III et al. | |
| 2007/0178776 | A1 * | 8/2007 | Etter et al. ................... | 439/877 |
| 2008/0097381 | A1 | 4/2008 | Moberg et al. | |
| 2008/0294108 | A1 | 11/2008 | Briones et al. | |
| 2009/0076461 | A1 | 3/2009 | Susi et al. | |
| 2009/0160654 | A1 | 6/2009 | Yang | |
| 2010/0063445 | A1 | 3/2010 | Sternberg et al. | |
| 2011/0208123 | A1 * | 8/2011 | Gray et al. ................... | 604/151 |

FOREIGN PATENT DOCUMENTS

| | | |
|---|---|---|
| EP | 0917882 A1 | 5/1999 |
| WO | 02/24257 A1 | 3/2002 |
| WO | 2004006981 A2 | 1/2004 |

OTHER PUBLICATIONS

Search Report from corresponding EP Appln. No. 10075446.4 dated Aug. 25, 2011 (10 pages).
Search Report from corresponding International Appln. No. PCT/US2011/030553 dated Dec. 23, 2011 (12 pages).

* cited by examiner

*Primary Examiner* — Nicholas Lucchesi
*Assistant Examiner* — Gerald Landry, II
(74) *Attorney, Agent, or Firm* — McCormick, Paulding & Huber LLP

(57) ABSTRACT

An infusion pump assembly includes an enclosure assembly. A reservoir assembly is positioned at least partially within the enclosure assembly and is configured to contain an infusible fluid. A pump assembly is positioned at least partially within the enclosure assembly and is configured to effectuate the dispensing of the infusible fluid contained within the reservoir assembly. Processing logic is positioned at least partially within the enclosure assembly and is configured to control the pump assembly. A removable cover assembly is configured to releasably engage the enclosure assembly. A combination of the removable cover assembly and at least a portion of the enclosure assembly defines a power supply cavity configured to prevent a removable power supply assembly from being reverse-polarity electrically coupled to the processing logic.

15 Claims, 5 Drawing Sheets

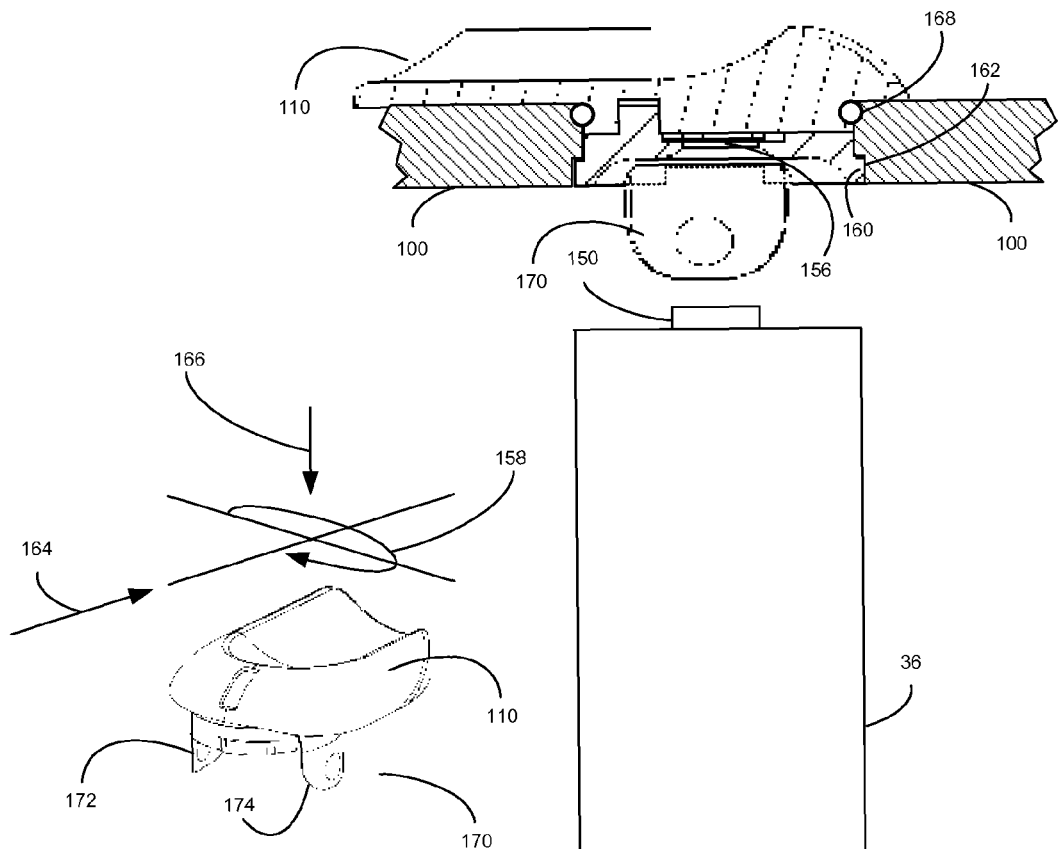
FIG. 4
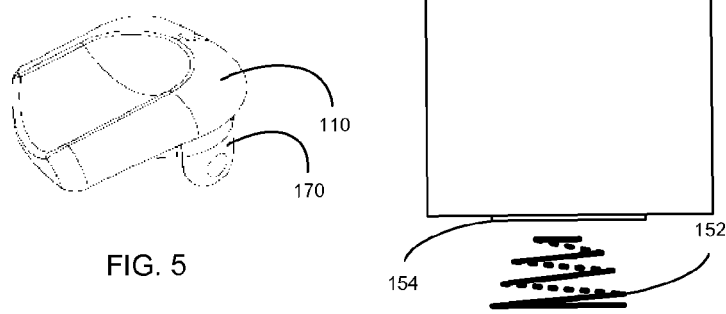
FIG. 5
FIG. 6

PUMP ASSEMBLY WITH A REMOVABLE COVER ASSEMBLY

CROSS REFERENCE TO RELATED APPLICATIONS

This application is a continuation of U.S. patent application Ser. No. 12/249,496, filed on Oct. 10, 2008, entitled "Pump Assembly with a Removable Cover Assembly" which is hereby incorporated herein by reference in its entirety.

TECHNICAL FIELD

This disclosure relates to infusion pump assemblies and, more particularly, to infusion pump assemblies that include serviceable battery assemblies.

BACKGROUND

An infusion pump assembly may be used to infuse a fluid (e.g., a medication or nutrient) into a user. The fluid may be infused intravenously (i.e., into a vein), subcutaneously (i.e., into the skin), arterially (i.e., into an artery), and epidurally (i.e., into the epidural space).

Infusion pump assemblies may administer fluids in ways that would be impracticably expensive/unreliable if performed manually by nursing staff. For example, an infusion pump assembly may repeatedly administer small quantities of an infusible fluid (e.g., 0.1 mL per hour), while allowing the user to request one-time larger "bolus" doses.

SUMMARY OF DISCLOSURE

In a first implementation, an infusion pump assembly includes an enclosure assembly. A reservoir assembly is positioned at least partially within the enclosure assembly and is configured to contain an infusible fluid. A pump assembly is positioned at least partially within the enclosure assembly and is configured to effectuate the dispensing of the infusible fluid contained within the reservoir assembly. Processing logic is positioned at least partially within the enclosure assembly and is configured to control the pump assembly. A removable cover assembly is configured to releasably engage the enclosure assembly. A combination of the removable cover assembly and at least a portion of the enclosure assembly defines a power supply cavity configured to prevent a removable power supply assembly from being reverse-polarity electrically coupled to the processing logic.

One or more of the following features may be included. The removable cover assembly may be configured to allow access to the power supply cavity and effectuate removable insertion of the removable power supply assembly into the power supply cavity. The removable power supply assembly may include a battery.

The removable cover assembly may include a sealing assembly for releasably engaging at least a portion of the enclosure assembly and forming an essentially water-tight seal between the removable cover assembly and the enclosure assembly. The sealing assembly may include an o-ring assembly. The removable cover assembly may include a conductor assembly configured to electrically couple the removable cover assembly with an interior wall of the power supply cavity.

The removable cover assembly may include a first twist lock assembly. The enclosure assembly may include a second twist lock assembly configured to releasably engage the first twist lock assembly and effectuate the releasable engagement of the removable cover assembly and the enclosure assembly.

In another implementation, an infusion pump assembly includes an enclosure assembly. A reservoir assembly is positioned at least partially within the enclosure assembly and is configured to contain an infusible fluid. A pump assembly is positioned at least partially within the enclosure assembly and is configured to effectuate the dispensing of the infusible fluid contained within the reservoir assembly. Processing logic is positioned at least partially within the enclosure assembly and is configured to control the pump assembly. A removable cover assembly is configured to releasably engage the enclosure assembly. The removable cover assembly includes a sealing assembly for releasably engaging at least a portion of the enclosure assembly and forming an essentially water-tight seal between the removable cover assembly and the enclosure assembly. A combination of the removable cover assembly and at least a portion of the enclosure assembly define a power supply cavity configured to allow removable insertion of a removable power supply assembly.

One or more of the following features may be included. The removable cover assembly may be configured to allow access to the power supply cavity and effectuate removable insertion of the removable power supply assembly into the power supply cavity. The removable power supply assembly may include a battery. The sealing assembly may include an o-ring assembly.

The removable cover assembly may include a conductor assembly configured to electrically couple the removable cover assembly with an interior wall of the power supply cavity. The removable cover assembly may include a first twist lock assembly. The enclosure assembly may include a second twist lock assembly configured to releasably engage the first twist lock assembly and effectuate the releasable engagement of the removable cover assembly and the enclosure assembly.

In another implementation, an infusion pump assembly includes an enclosure assembly. A reservoir assembly is positioned at least partially within the enclosure assembly and is configured to contain an infusible fluid. A pump assembly is positioned at least partially within the enclosure assembly and is configured to effectuate the dispensing of the infusible fluid contained within the reservoir assembly. Processing logic is positioned at least partially within the enclosure assembly and is configured to control the pump assembly. A removable cover assembly, which is configured to releasably engage the enclosure assembly, includes a first twist lock assembly. A combination of the removable cover assembly and at least a portion of the enclosure assembly define a power supply cavity configured to allow removable insertion of a removable power supply assembly. The enclosure assembly includes a second twist lock assembly configured to releasably engage the first twist lock assembly and effectuate the releasable engagement of the removable cover assembly and the enclosure assembly.

One or more of the following features may be included. The removable cover assembly may be configured to allow access to the power supply cavity and effectuate removable insertion of the removable power supply assembly into the power supply cavity. The removable power supply assembly may include a battery. The removable cover assembly may include a conductor assembly configured to electrically couple the removable cover assembly with an interior wall of the power supply cavity.

In another implementation, an infusion pump assembly includes an enclosure assembly. A reservoir assembly is positioned at least partially within the enclosure assembly and is configured to contain an infusible fluid. A pump assembly is positioned at least partially within the enclosure assembly and is configured to effectuate the dispensing of the infusible fluid contained within the reservoir assembly. Processing logic is positioned at least partially within the enclosure assembly and is configured to control the pump assembly. A removable cover assembly is configured to releasably engage the enclosure assembly. A combination of the removable cover assembly and at least a portion of the enclosure assembly defines a power supply cavity configured to allow removable insertion of the removable power supply assembly. The removable cover assembly includes a conductor assembly configured to electrically couple the removable cover assembly with an interior wall of the power supply cavity.

One or more of the following features may be included. The removable cover assembly may be configured to allow access to the power supply cavity and effectuate removable insertion of the removable power supply assembly into the power supply cavity. The removable power supply assembly may include a battery.

The details of one or more implementations are set forth in the accompanying drawings and the description below. Other features and advantages will become apparent from the description, the drawings, and the claims.

BRIEF DESCRIPTION OF THE DRAWINGS

FIG. 4 is an isometric view of a removable cover assembly for use with the infusion pump assembly of FIG. 2;

FIG. 5 is an alternative isometric view of the removable cover assembly of FIG. 4;

FIG. 6 is a cross-sectional view of the removable cover assembly of FIG. 4;

Like reference symbols in the various drawings indicate like elements.

DETAILED DESCRIPTION OF THE PREFERRED EMBODIMENTS

Figure 1:
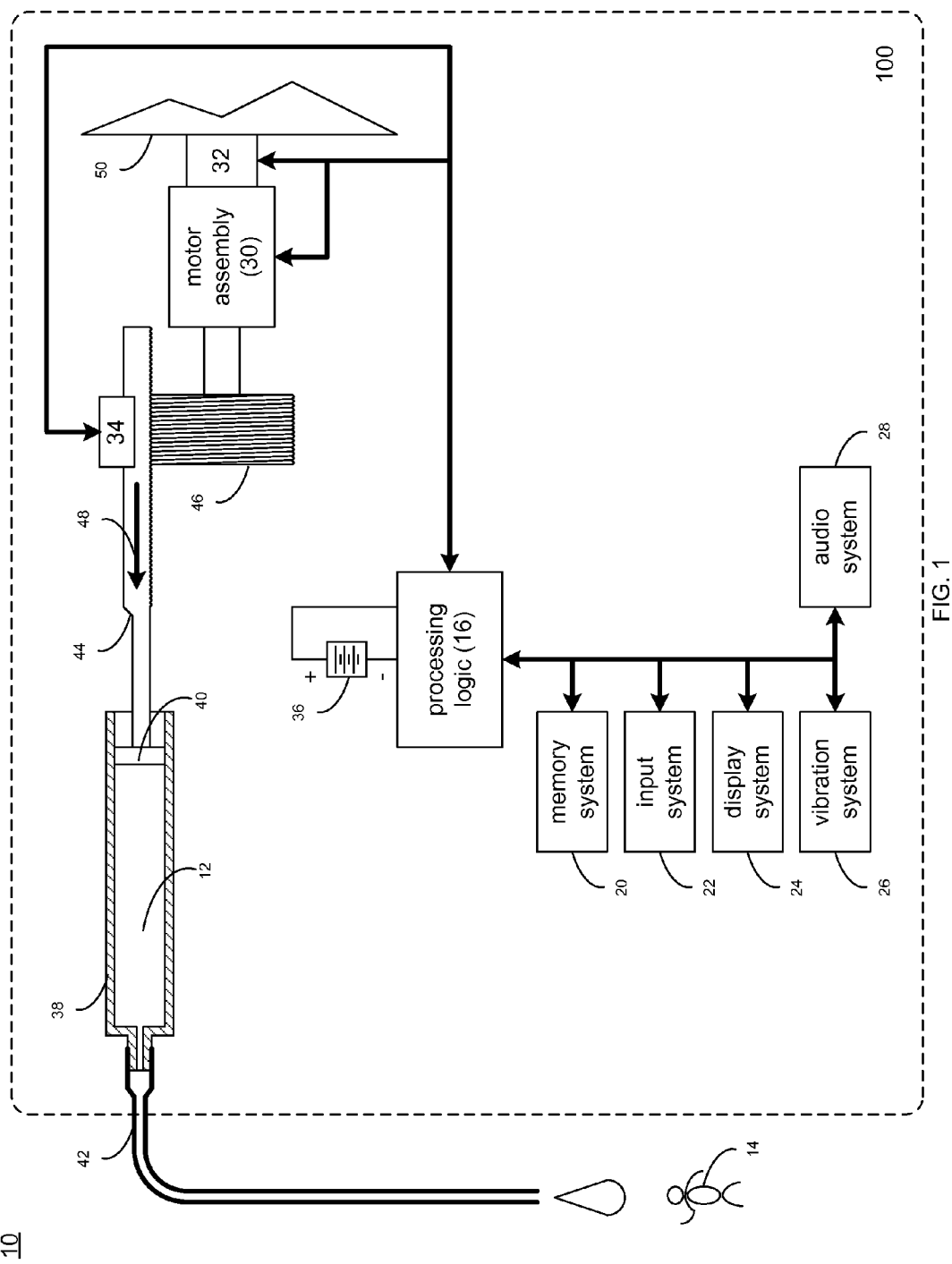
FIG. 1 is a diagrammatic view of an infusion pump assembly.

Referring to FIG. 1, there is shown in infusion pump assembly 10 that may be configured to deliver infusible fluid 12 to user 14. As discussed above, infusible fluid 12 may be delivered intravenously (i.e., into a vein), subcutaneously (i.e., into the skin), arterially (i.e., into an artery), and epidurally (i.e., into the epidural space). Examples of infusible fluid 12 may include but are not limited to insulin, nutrients, saline solution, antibiotics, analgesics, anesthetics, hormones, vasoactive drugs, and chelation drugs, and any other therapeutic fluids.

Infusion pump assembly 10 may include processing logic 16 that executes one or more processes that may be required for infusion pump assembly 10 to operate properly. Processing logic 16 may include one or more microprocessors (not shown), one or more input/output controllers (not shown), and cache memory devices (not shown). One or more data buses and/or memory buses may be used to interconnect processing logic 16 with one or more subsystems.

Examples of the subsystems interconnected with processing logic 16 may include but are not limited to memory system 20, input system 22, display system 24, vibration system 26, audio system 28, motor assembly 30, force sensor 32, and displacement detection device 34. Infusion pump assembly 10 may include removable power supply assembly 36 (e.g. a battery) for providing electrical power to at least a portion of processing logic 16 and one or more of the subsystems (e.g., memory system 20, input system 22, display system 24, vibration system 26, audio system 28, motor assembly 30, force sensor 32, and displacement detection device 34).

Infusion pump assembly 10 may include reservoir assembly 38 configured to contain infusible fluid 12. In some embodiments, the reservoir assembly 38 may be a reservoir assembly similar to that described in U.S. Patent Application Publication No. US 2004-0135078-A1, published Jul. 15, 2004, which is herein incorporated by reference in its entirety. In other embodiments, the reservoir assembly may be any assembly in which fluid may be acted upon such that at least a portion of the fluid may flow out of the reservoir assembly, for example, the reservoir assembly, in various embodiments, may include but is not limited to: a barrel with a plunger, a cassette or a container at least partially constructed of a flexible membrane.

Plunger assembly 40 may be configured to displace infusible fluid 12 from reservoir assembly 38 through cannula assembly 42 so that infusible fluid 12 may be delivered to user 14. In this particular embodiment, plunger assembly 40 is shown to be displaceable by partial nut assembly 44, which may engage lead screw assembly 46 that may be rotatable by motor assembly 30 in response to signals received from processing logic 16. In this particular embodiment, the combination of motor assembly 30, plunger assembly 40, partial nut assembly 44, and lead screw assembly 46 may form a pump assembly that effectuates the dispensing of infusible fluid 12 contained within reservoir assembly 38. An example of partial nut assembly 44 may include but is not limited to a nut assembly that is configured to wrap around lead screw assembly 46 by e.g., 30 degrees. In some embodiments, the pump assembly may be similar to one described in U.S. Pat. No. 7,306,578 issued Dec. 11, 2007 which is herein incorporated by reference in its entirely.

During operation of infusion pump assembly 10, infusible fluid 12 may be delivered to user 14 in accordance with e.g. a defined delivery schedule. For illustrative purposes only, assume that infusion pump assembly 10 is configured to provide 0.00025 mL of infusible fluid 12 to user 14 every three minutes. Accordingly, every three minutes, processing logic 16 may provide the appropriate drive signals to motor assembly 30 to allow motor assembly 30 to rotate lead screw assembly 46 the appropriate amount so that partial nut assembly 44 (and therefore plunger assembly 40) may be displaced the appropriate amount in the direction of arrow 48 so that 0.00025 mL of infusible fluid 12 are provided to user 14 (via cannula 42). It should be understood that the volume of infusible fluid 12 that may be provided to user 14 may vary based upon, at least in part, the nature of the infusible fluid (e.g., the type of fluid, concentration, etc.), use parameters (e.g., treatment type, dosage, etc.), as well as various other factors that will be understood by one having skill in the art. As such, the foregoing illustrative example should not be construed as a limitation of the present disclosure.

Force sensor 32 may be configured to provide processing logic 16 with data concerning the force required to drive plunger assembly 40 into reservoir assembly 38. Force sensor 32 may include one or more strain gauges and/or pressure sensing gauges and may be positioned between motor assembly 30 and an immovable object (e.g. bracket assembly 50) included within infusion pump assembly 10.

In one embodiment, force sensor 32 includes four strain gauges (not shown), such that: two of the four strain gauges are configured to be compressed when driving plunger 40 into reservoir assembly 38; and two of the four strain gauges are configured to be stretched when driving plunger 40 into reservoir assembly 38. The four strain gauges (not shown) may be connected to a Wheatstone Bridge (not shown) that produces an analog force signal (not shown) that is a function of the pressure sensed by force sensor 32. The analog force signal (not shown) produced by force sensor 32 may be provided to an analog-to-digital converter (not shown) that may convert the analog force signal (not shown) into a digital force signal (not shown) that may be provided to processing logic 16. An amplifier assembly (not shown) may be positioned prior to the above-described analog-to-digital converter and may be configured to amplify the output of e.g., force sensor 32 to a level sufficient to be processed by the above-described analog-to-digital converter.

Motor assembly 30 may be configured as e.g., a brush-type DC electric motor. Further, motor assembly 30 may include a reduction gear assembly (not shown) that e.g. requires motor assembly 30 to rotate three-thousand revolutions for each revolution of lead screw assembly 46, thus increasing the torque and resolution of motor assembly 30 by a factor of three-thousand.

As discussed above, infusion pump assembly 10 may be configured to deliver infusible fluid 12 to user 14. Infusible fluid 12 may be delivered to user 14 via one or more different infusion event types. For example, infusion pump assembly 10 may deliver infusible fluid 12 via a sequential, multi-part, infusion event (that may include a plurality of discrete infusion events) and/or a one-time infusion event.

Examples of such a sequential, multi-part, infusion event may include but are not limited to a basal infusion event and an extended-bolus infusion event. As is known in the art, a basal infusion event refers to the repeated injection of small (e.g. 0.05 unit) quantities of infusible fluid 12 at a predefined interval (e.g. every three minutes) that is repeated. Further, the basal infusion rates may be pre-programmed and may include specified rates for pre-programmed time-frames, e.g., a rate of 0.50 units per hour from 6 am-3 pm; a rate of 0.40 units per hour from 3 pm-10 pm; and a rate of 0.35 units per hour from 10 pm-6 am. However, similarly, the basal rate may be 0.025 units per hour, and may not change according to pre-programmed time-frames. The basal rates may be repeated regularly/daily until otherwise changed.

Further and as is known in the art, an extended-bolus infusion event refers to the repeated injection of small (e.g. 0.025 unit) quantities of infusible fluid 12 at a predefined interval (e.g. every three minutes) that is repeated for a defined number of intervals (e.g., three intervals) or for a defined period of time (e.g., one hour). An extended-bolus infusion event may occur simultaneously with a basal infusion event.

In contrast, as is known in the art, a normal bolus infusion event refers to a one-time infusion of infusible fluid 12. The volume of the infusible fluid 12 delivered in a bolus infusion event may be requested, and infusion pump assembly 10 may deliver the requested volume of infusible fluid 12 for the bolus infusion event at a predetermined rate (e.g., as quickly as the infusion pump assembly can deliver). However, the infusion pump assembly may deliver a normal bolus at a slower rate where the normal bolus volume is greater than a pre-programmed threshold.

Referring also to FIGS. 2, 2L, 2R & 3, the above-described components of infusion pump assembly 10 may be included within enclosure assembly 100. Enclosure assembly 100 may be configured so that display system 24 is visible by user 14 through enclosure assembly 100. One or more switch assemblies/input devices 102, 104, 106 (included within input system 22) may be positioned about various portions of enclosure assembly 100. Enclosure assembly 100 may include infusion port assembly 108 to which cannula assembly 42 may be releasably coupled. A combination of removable cover assembly 110 and a portion of enclosure assembly 100 may define power supply cavity 112 (shown in phantom on FIG. 2).

Referring also to FIGS. 4-6, power supply cavity 112 (which is formed by a combination of removable cover assembly 110 and a portion of enclosure assembly 100) may be configured to releasably receive removable power supply assembly 36. Additionally, power supply cavity 112 may be configured to prevent removable power supply assembly 36 from being reverse-polarity electrically coupled to processing logic 16. For example, power supply cavity 112 may be configured to prevent positive terminal 150 of removable power supply assembly 36 from being electrically coupled to negative terminal 152 of power supply cavity 112 and/or negative terminal 154 of removable power supply 36 from being electrically coupled to positive terminal 156 of power supply cavity 112).

Configuring power supply cavity 112 to prevent removable power supply 36 from being reverse-polarity electrically coupled to processing logic 16 may provide various benefits. For example, the configuration may prevent the loss of power from the removable power supply assembly 36 (e.g., discharge of the battery) where the removable power supply assembly 36 has been inserted incorrectly. In addition to functioning to not waste power, this configuration may also be a safety feature to infusion pump assembly 10. Infusion pump assembly 10 may rely on power for functionality. A user may rely on infusion pump assembly 10 to provide life-sustaining therapy, for example, by delivering insulin. Thus, preventing removable power supply assembly 36 from being reverse-polarity electrically coupled to processing logic 16 (e.g., as a result of user 14 having mistakenly inserted removable power supply assembly 36 incorrectly), preventing removable power supply 36 from being reverse-polarity electrically coupled to processing logic 16 may allow infusion pump assembly 10 to function for a longer time than if the incorrectly installed removable power supply assembly 36 had been able to be reverse-polarity electrically coupled to processing logic 16.

Removable cover assembly 110 may be configured to allow access to power supply cavity 112 and effectuate the installation/replacement/removal of removable power supply assembly 36. As discussed above, an example of removable power supply assembly 36 may include but is not limited to a battery. In some embodiments, the battery may include, but is not limited to, an A, AA, AAA or AAAA battery, and the battery may be a lithium battery or alkaline battery. The battery may, in some embodiments, be a rechargeable battery.

Removable cover assembly 110 may be configured to rotatably engage enclosure assembly 100 in the direction of arrow 158. For example, removable cover assembly 110 may include first twist lock assembly 160 (e.g., a protruding tab). Enclosure assembly 100 may include a second twist lock assembly 162 (e.g., a slot) configured to releasably engage first twist lock assembly and effectuate the releasable engagement of the removable cover assembly and the enclosure assembly.

While removable cover assembly 110 and enclosure assembly 100 is described above as including first twist lock assembly 160 and second twist lock assembly 162, this is for illustrative purposes only and is not intended to be a limitation of this disclosure, as other configurations are possible and are considered to be within the scope of this disclosure. For example, one or more thread assemblies (not shown) may be utilized to effectuate the above-described rotatable engagement.

Further, while removable cover assembly 110 is described above as being configured to rotatably engage enclosure assembly 100, this is for illustrative purposes only and is not intended to be a limitation of this disclosure, as other configurations are possible. For example, removable cover assembly 110 may be configured to slidably engage enclosure assembly 100 (in the direction of arrow 164) using a slide assembly (not shown). Alternatively, removable cover assembly 110 may be configured to be pressed into enclosure assembly 100 in the direction of arrow 166.

Removable cover assembly 110 may include sealing assembly 168 (e.g., an o-ring assembly) that is configured to releasably engage at least a portion of enclosure assembly 100 to form an essentially water-tight seal between removable cover assembly 110 and enclosure assembly 100.

In an embodiment in which sealing assembly 168 includes an o-ring assembly included within removable cover assembly 110, the o-ring assembly may be sized to effectuate a watertight (or essentially watertight) seal with a corresponding surface of enclosure assembly 100.

Alternatively, in an embodiment in which sealing assembly 168 includes an o-ring assembly included within enclosure assembly 100, the o-ring assembly may be sized to effectuate a watertight (or essentially watertight) seal with a corresponding surface of removable cover assembly 110.

Figure 7:
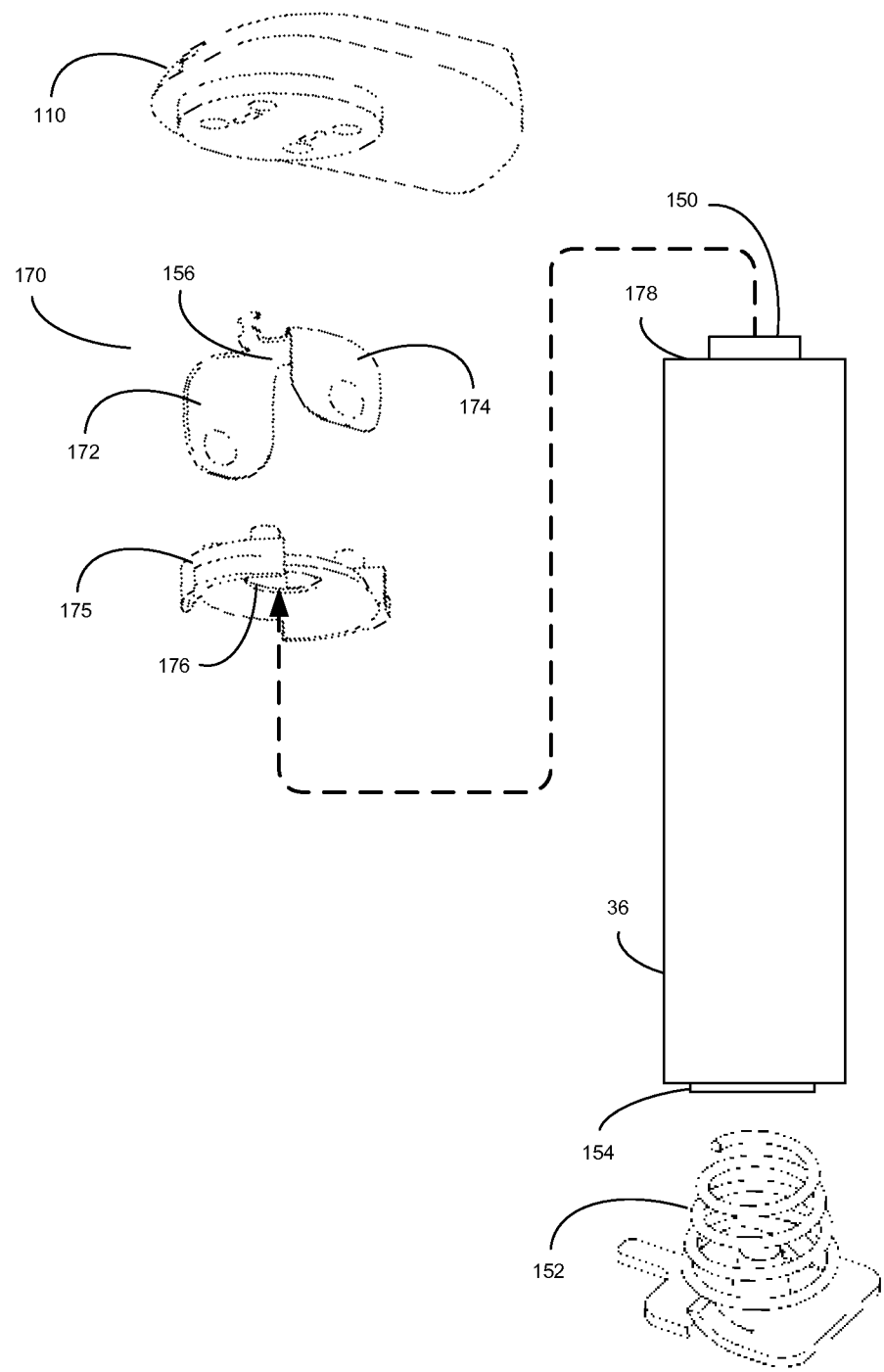
FIG. 7 is an alternative isometric view of the removable cover assembly of FIG. 4.
Figure 8A:
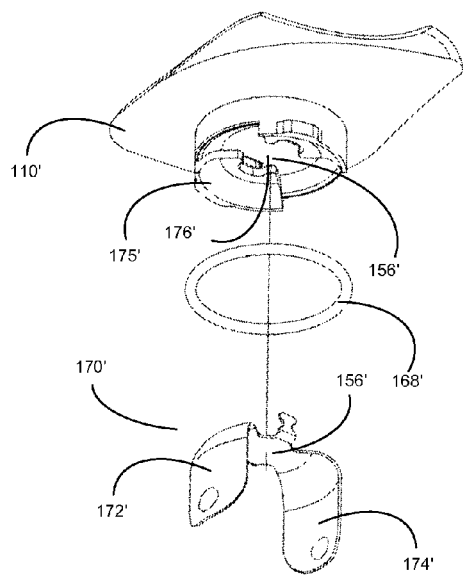
FIG. 8A-8D are isometric views of an alternative embodiment of the removable cover assembly of FIG. 4.
Figure 8B:
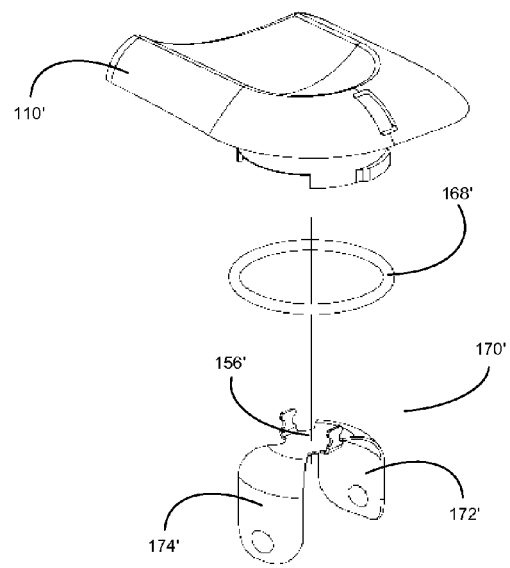
Figure 8C:
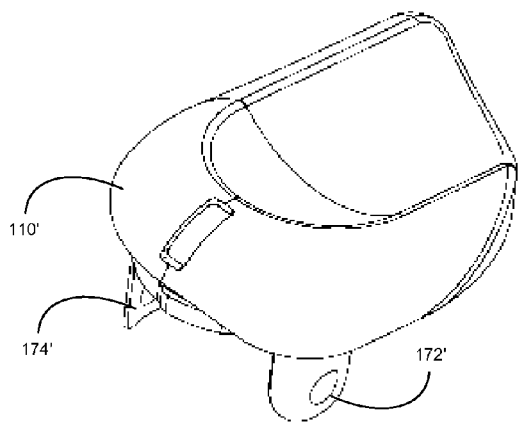
Figure 8D:
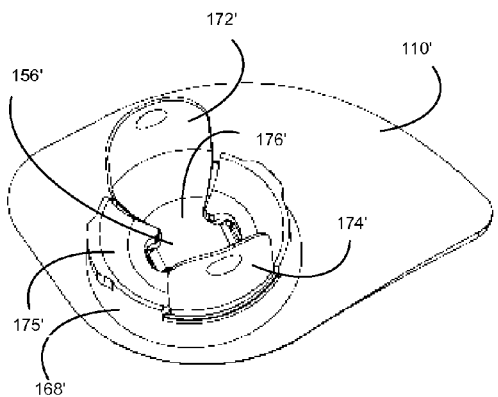

Removable cover assembly 110 may include conductor assembly 170 for electrically coupling positive terminal 156 of removable cover assembly 110 with interior wall 114 of power supply cavity 112. For example, conductor assembly 170 may include a plurality of tabs (e.g., tabs 172, 174) that may be electrically coupled to positive terminal 156 of removable cover assembly 110. Tabs 172, 174 may be configured so that when removable cover assembly 110 releasably engages enclosure assembly 100, tabs 172, 174 may make electrical contact with interior wall 114 of power supply cavity 112. Interior wall 114 of power supply cavity 112 may then be electrically coupled to the various components within infusion pump assembly 10 that require electrical power, examples of which may include but are not limited to processing logic 16, As discussed above, the combination of removable cover assembly 110 and a portion of enclosure assembly 100 may be configured to prevent removable power supply assembly 36 from being reverse-polarity electrically coupled to processing logic 16. Referring also to FIG. 7, one or more of negative terminal 152 and positive terminal 156 may be configured so that the above-described reverse polarity situation cannot occur. For example, removable cover assembly 110 may include insulator assembly 175 that includes recess 176 that is sized to receive positive terminal 150 of removable power supply assembly 36 and enable electrical contact with positive terminal 156 of removable cover assembly 110. Insulator assembly 175 may be constructed of an insulating material, for example, but limited to, plastic, for example, but not limited to, PVC plastic or bakelite. Further, recess 176 may be sized so that negative terminal 154 of removable power supply assembly 36 cannot make electrical contact with positive terminal 156 (and may only make contact with insulator 176), thus preventing removable power supply assembly 36 from being electrically coupled to processing logic 16 in a reverse-polarity configuration.

Referring also to FIGS. 8A-8D, there is shown an alternative-embodiment removable cover assembly 110'. Removable cover assembly 110' may include sealing assembly 168' (e.g., an o-ring assembly) that is configured to releasably engage at least a portion of enclosure assembly 100 to form an essentially water-tight seal between removable cover assembly 110' and enclosure assembly 100.

Figure 2R:
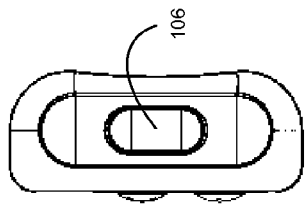
FIG. 2R is a right-side view of the infusion pump assembly of FIG. 2.
Figure 2:
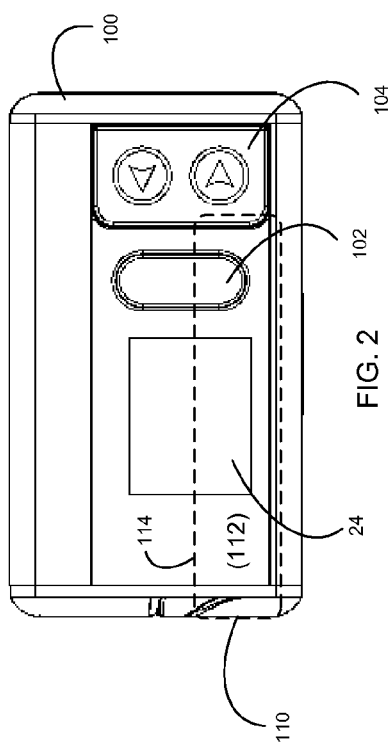
FIG. 2 is a front view of the infusion pump assembly of FIG. 1.
Figure 2L:
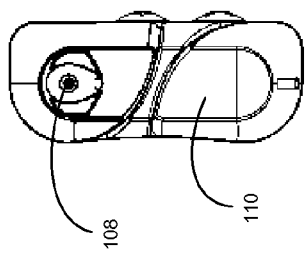
FIG. 2L is a left-side view of the infusion pump assembly of FIG. 2.
Figure 3:
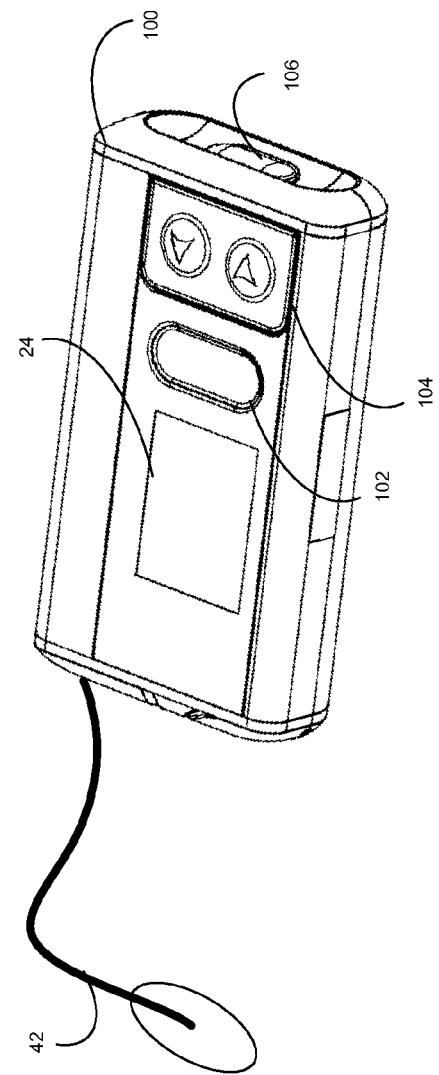
FIG. 3 is an isometric view of the infusion pump assembly of FIG. 2.

Removable cover assembly 110 may include conductor assembly 170' for electrically coupling positive terminal 156' of removable cover assembly 110' with interior wall 114 (FIG. 2) of power supply cavity 112 (FIG. 2). For example, conductor assembly 170' may include a plurality of tabs (e.g., tabs 172', 174') that may be electrically coupled to positive terminal 156' of removable cover assembly 110'. Tabs 172', 174' may be configured so that when removable cover assembly 110' releasably engages enclosure assembly 100 (FIG. 2), tabs 172', 174' may make electrical contact with interior wall 114 of power supply cavity 112. Interior wall 114 of power supply cavity 112 may then be electrically coupled to the various components within infusion pump assembly 10 that require electrical power, examples of which may include but are not limited to processing logic 16, As discussed above, the combination of removable cover assembly 110' and a portion of enclosure assembly 100 may be configured to prevent removable power supply assembly 36 from being reverse-polarity electrically coupled to processing logic 16. For example, removable cover assembly 110' may include insulator assembly 175' that defines recess 176' that is sized to receive positive terminal 150 (FIGS. 6-7) of removable power supply assembly 36 (FIGS. 6-7) and enable electrical contact with positive terminal 156' of removable cover assembly 110'. Insulator assembly 175', which may be constructed of an insulating material (which in some embodiments may include, but is not limited to plastic, which may include, but is not limited to, PVC plastic or bakelite), may be molded into and/or a portion of removable cover assembly 110'. Further, recess 176' may be sized so that negative terminal 154 (FIGS. 6-7) of removable power supply assembly 36 cannot make electrical contact with positive terminal 156' (and may only make electrical contact with insulator 176', thus preventing removable power supply assembly 36 from being electrically coupled to processing logic 16 in a reverse-polarity configuration.

While power supply cavity 112 is described above as having positive terminal 156 positioned proximate removable cover assembly 110, this is for illustrative purposes only and is not intended to be a limitation of this disclosure, as other configurations are possible and are considered to be within the scope of this disclosure. For example, negative terminal 152 may be positioned proximate removable cover assembly 110.

A number of implementations have been described. Nevertheless, it will be understood that various modifications may be made. Accordingly, other implementations are within the scope of the following claims.

What is claimed is:
1. An infusion pump assembly comprising:
an enclosure assembly;
a reservoir assembly positioned at least partially within the enclosure assembly and configured to contain an infusible fluid;

a pump assembly positioned at least partially within the enclosure assembly and configured to effectuate the dispensing of the infusible fluid contained within the reservoir assembly;

processing logic positioned at least partially within the enclosure assembly and configured to control the pump assembly; and a removable cover assembly configured to releasably engage the enclosure assembly;

wherein a combination of the removable cover assembly and at least a portion of the enclosure assembly define a power supply cavity, the combination preventing a removable power supply assembly within the power supply cavity from being reverse-polarity electrically coupled to the processing logic.

2. The infusion pump assembly of claim 1 wherein the removable cover assembly covers an access opening when engaging the enclosure assembly that allows access to the power supply cavity and effectuates removable insertion of the removable power supply assembly into the power supply cavity.

3. The infusion pump assembly of claim 1 wherein the removable power supply assembly includes a battery.

4. The infusion pump assembly of claim 1 wherein the removable cover assembly includes:
a sealing assembly for releasably engaging at least a portion of the enclosure assembly and forming an essentially water-tight seal between the removable cover assembly and the enclosure assembly.

5. The infusion pump assembly of claim 4 wherein the sealing assembly includes an o-ring assembly.

6. The infusion pump assembly of claim 1 wherein the removable cover assembly includes:
a conductor assembly configured to electrically couple the removable cover assembly with an interior wall of the power supply cavity.

7. An infusion pump assembly comprising:
an enclosure assembly;
a reservoir assembly positioned at least partially within the enclosure assembly and configured to contain an infusible fluid;
a pump assembly positioned at least partially within the enclosure assembly and configured to effectuate the dispensing of the infusible fluid contained within the reservoir assembly;
processing logic positioned at least partially within the enclosure assembly and configured to control the pump assembly; and
a removable cover assembly configured to releasably engage the enclosure assembly, the removable cover assembly including a sealing assembly for releasably engaging at least a portion of the enclosure assembly and forming an essentially water-tight seal between the removable cover assembly and the enclosure assembly;
wherein a combination of the removable cover assembly and at least a portion of the enclosure assembly define a power supply cavity configured to allow removable insertion of a removable power supply assembly, the combination preventing the removable power supply assembly within the power supply cavity from being reverse-polarity electrically coupled to the processing logic, the power supply cavity having an access opening that is covered by the removable cover assembly when engaged with the enclosure assembly; and
wherein the sealing assembly substantially surrounds the access opening.

8. The infusion pump assembly of claim 7 wherein the removable cover assembly is configured to allow access to the power supply cavity and effectuate removable insertion of the removable power supply assembly into the power supply cavity.

9. The infusion pump assembly of claim 7 wherein the removable power supply assembly includes a battery.

10. The infusion pump assembly of claim 7 wherein the sealing assembly includes an o-ring assembly.

11. The infusion pump assembly of claim 7 wherein the removable cover assembly includes:
a conductor assembly configured to electrically couple the removable cover assembly with an interior wall of the power supply cavity.

12. An infusion pump assembly comprising:
an enclosure assembly;
a reservoir assembly positioned at least partially within the enclosure assembly and configured to contain an infusible fluid;
a pump assembly positioned at least partially within the enclosure assembly and configured to effectuate the dispensing of the infusible fluid contained within the reservoir assembly;
processing logic positioned at least partially within the enclosure assembly and configured to control the pump assembly; and
a removable cover assembly configured to releasably engage the enclosure assembly, the removable cover assembly including a first twist lock assembly having at least one tab;
wherein a combination of the removable cover assembly and at least a portion of the enclosure assembly define a power supply cavity configured to allow removable insertion of a removable power supply assembly; and
wherein the enclosure assembly includes a second twist lock assembly having at least one slot configured to releasably engage the at least one tab of the first twist lock assembly and effectuate the releasable engagement of the removable cover assembly and the enclosure assembly.

13. The infusion pump assembly of claim 12 wherein the removable cover assembly is configured to allow access to the power supply cavity and effectuate removable insertion of the removable power supply assembly into the power supply cavity.

14. The infusion pump assembly of claim 12 wherein the removable power supply assembly includes a battery.

15. The infusion pump assembly of claim 12 wherein the removable cover assembly includes:
a conductor assembly configured to electrically couple the removable cover assembly with an interior wall of the power supply cavity.

* * * * *